(12) United States Patent
Angelini et al.

(10) Patent No.: US 9,518,047 B2
(45) Date of Patent: Dec. 13, 2016

(54) PROCESS FOR THE INDUSTRIAL SYNTHESIS OF LURASIDONE

(71) Applicant: PROCOS S.P.A., Cameri (IT)

(72) Inventors: Tommaso Angelini, Oleggio (IT); Piergiorgio Bettoni, Casale Monferrato (IT); Jacopo Roletto, Turin (IT); Paolo Paissoni, Druento (IT)

(73) Assignee: PROCOS S.P.A., Cameri (NO) (IT)

( * ) Notice: Subject to any disclaimer, the term of this patent is extended or adjusted under 35 U.S.C. 154(b) by 0 days.

(21) Appl. No.: 15/028,962

(22) PCT Filed: Oct. 16, 2014

(86) PCT No.: PCT/IB2014/065361
§ 371 (c)(1),
(2) Date: Apr. 13, 2016

(87) PCT Pub. No.: WO2015/056205
PCT Pub. Date: Apr. 23, 2015

(65) Prior Publication Data
US 2016/0237077 A1 Aug. 18, 2016

(30) Foreign Application Priority Data
Oct. 17, 2013 (IT) .............................. MI2013A1737

(51) Int. Cl.
*C07D 417/12* (2006.01)
(52) U.S. Cl.
CPC ................... *C07D 417/12* (2013.01)
(58) Field of Classification Search
None
See application file for complete search history.

(56) References Cited

U.S. PATENT DOCUMENTS 5,532,372 A 7/1996 Saji et al.

FOREIGN PATENT DOCUMENTS

| WO | 2011002103 A2 | 1/2011 |
| WO | 2012131606 A1 | 10/2012 |
| WO | 2013132511 A1 | 9/2013 |

OTHER PUBLICATIONS

International Search Report and Written Opinion of PCT/IB2014/065361 of Jan. 7, 2015.

*Primary Examiner* — Emily Bernhardt
(74) *Attorney, Agent, or Firm* — Silvia Savadori, P.C.; Silvia Salvadori

(57) ABSTRACT

Disclosed is a process for the industrial synthesis of Lurasidone from (1R,2R)-cyclohexane-1,2-diyldimethanol (1), 3-(piperazin-1-yl)benzo[d]isothiazole (3) and (3aR,4R,7R,7aS)-3a,4,7,7a-tetrahydro-4,7-methanoisobenzofuran-1,3-dione (6).). Said process is optimised to obtain Lurasidone with high yields and high purities by preparing highly pure synthesis intermediates, using critical raw materials and reagents in amounts close to the stoichiometric amounts, increasing productivity and reducing the costs and environmental impact of the process.

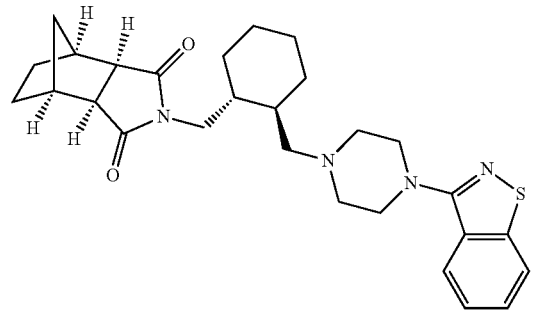

LURASIDONE

6 Claims, No Drawings

PROCESS FOR THE INDUSTRIAL SYNTHESIS OF LURASIDONE

This application is a U.S. national stage of PCT/IB2014/065361 filed on 16 Oct. 2014, which claims priority to and the benefit of Italian Application No. MI2013A001737 filed on 17 Oct. 2013, the contents of which are incorporated herein by reference in their entireties.

SUMMARY OF THE INVENTION

The present invention relates to a process for the industrial synthesis of Lurasidone from (1R,2R)-cyclohexane-1,2-diyldimethanol (1), 3-(piperazin-1-yl)benzo[d]isothiazole (3) and (3aR,4R,7R,7aS)-3a,4,7,7a-tetrahydro-4,7-methanoisobenzofuran-1,3-dione (6).

BACKGROUND OF THE INVENTION

Lurasidone, [(3aR,4S,7S,7aS)-2-(((1R,2R)-2-((4-(benzo[d]isothiazol-3-yl)piperazin-1-yl)methyl)cyclohexyl)methyl)hexahydro-1H-4,7-methanoisoindole-1,3(2H)-dione], is a new-generation atypical antipsychotic drug used in the treatment of schizophrenia, bipolar disorder and other psychiatric conditions. Lurasidone acts as a serotonin/dopamine receptor (5-HT$_{2A}$/D$_2$) antagonist.

U.S. Pat. No. 5,532,372 discloses the synthesis of racemic Lurasidone from trans-cyclohexane-1,2-diyldimethanol (rac-1) (Scheme 1).

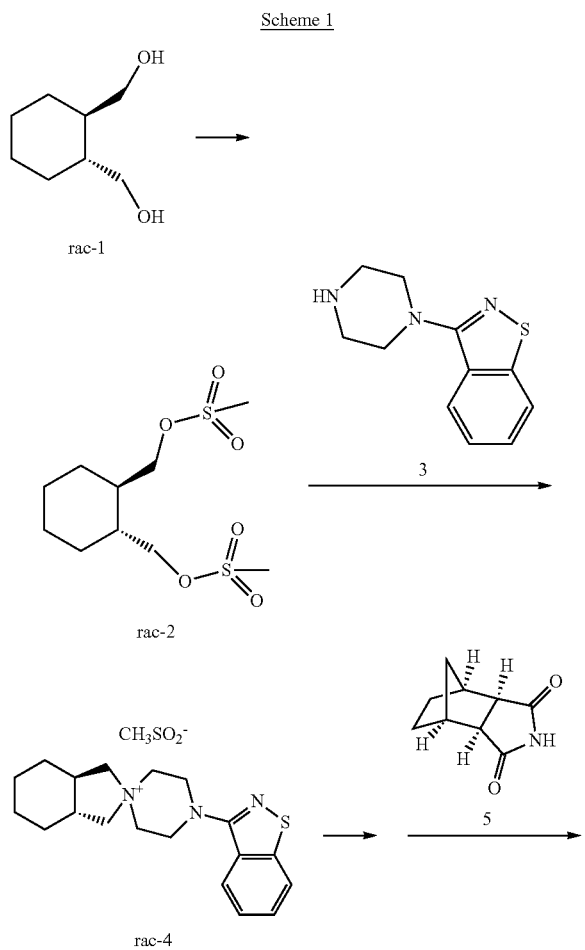

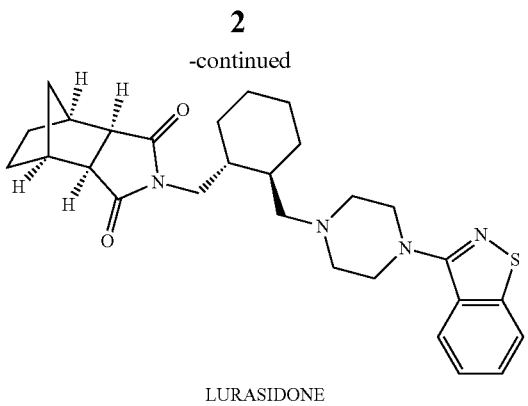

LURASIDONE
RACEMIC MIXTURE

SYNTHESIS OF LURASIDONE (FROM US5532372)

Lurasidone can be obtained as a single enantiomer after chiral resolution by crystallisation with L-tartaric acid.

According to said patent, each single intermediate is isolated; the process involves the use of expensive solvents, such as acetonitrile, or solvents which are not industrially suitable, such as diethyl ether. Said process also involves the use of expensive catalysts such as crown ethers, and chromatographic purification which is difficult to apply on an industrial scale. The mesylation step used to give the intermediate rac-2 presents a low yield, and the intermediate rac-2 is used in the subsequent reaction in excess, involving a cost increase. The patent reports a quantitative yield in the rac-4 intermediate formation step, but the yields reported in the subsequent literature (see below) and experimental tests demonstrate that lower yields (80-88%) are obtained under the same reaction conditions, due to the decomposition of rac-2 promoted by strong bases such as potassium carbonate used in excess, to give decomposition products undetectable by UV detectors.

Another evident drawback of this process is that enantiopure Lurasidone has to be isolated at the end of the process from a racemic mixture with a resolution by crystallisation, followed by a further salification and crystallisation, considerably increasing the costs and environmental impact of the process.

The patent does not disclose the synthesis of imide intermediate 5 used in the last synthesis step, in reaction with the intermediate rac-4, to obtain Lurasidone racemate.

The synthesis of Lurasidone from enantiopure compounds is disclosed in WO 2012131606 and IPCOM000204532D, using the procedures and reagents reported in U.S. Pat. No. 5,532,372, and thus suffering from the same limitations and lower yields in the formation of intermediate 4 (88%).

Other patents disclose, in particular, the step involving formation of intermediate 4, which is a critical step in the synthesis of Lurasidone.

US2011003994 reports the preparation of intermediate 4 in acetonitrile in the presence of potassium carbonate, with the same procedure as used in U.S. Pat. No. 5,532,372. A similar procedure, wherein acetonitrile is used as the solvent and potassium carbonate as the base, is described in IPCOM000205160D. In both these cases the most expensive intermediate, mesylate 2, is used in a slight excess (1.02 to 1.05 molar equivalents of intermediate 2 are reacted with 1.00 molar equivalents of intermediate 3), and the yields are low (80%).

US20110263847, filed by the owner of U.S. Pat. No. 5,532,372, describes the preparation of intermediate 4 and its subsequent reaction with imide intermediate 5 to give Lurasidone. This document indicates the low yield and presence of impurities in the methods previously reported. According to the invention claimed in US20110263847, mesylate 2 is reacted in toluene with a large excess (1.5 to 15 equivalents) of amine 3. The use of this excess is justified by higher yields and purities than the preceding methods, although no procedure involves isolating products, only a study of the reaction mixtures using HPLC analysis. However, the use of a large excess of 3, both as nucleophile and as base to neutralise the methanesulfonic acid formed, involves a considerable economic cost, and the excess remains in the reaction mixture as ammonium salt, which is liable to contaminate the end product.

Similarly, US20110263848, also filed by the owner of U.S. Pat. No. 5,532,372, discloses the preparation of intermediate 4 and its subsequent reaction with imide intermediate 5 to give Lurasidone. That document indicates the low yield and the presence of impurities in the methods previously reported. According to the invention claimed in US20110263848, mesylate 2 is reacted with amine 3 in toluene, in the presence of a dibasic or tribasic phosphate and a small amount of water. Once again, the procedure for isolating the products is not described, and the yields and purities are calculated by HPLC analysis of the reaction mixtures. Although in this case too the HPLC purities of the reaction mixtures are higher than those of the procedures previously reported, said method still uses an excess of mesylate 2 to complete the reaction. The use of said excess is not only a drawback from the economic standpoint but also involves potential contamination of the product with mesylate 2 and other impurities undetectable by the normal UV detectors of HPLC instruments. Continuing the synthesis of Lurasidone in the same reaction solvent, without isolating intermediate 4, therefore involves potential pollution by substances undetectable by UV detectors.

The preparation of imide intermediate 5 is not reported in any process patent for the synthesis of Lurasidone. It can be prepared by hydrogenation of intermediate 7, deriving from anhydride 6, or from maleimide 8 by reaction with cyclopentadiene 9 (Scheme 2).

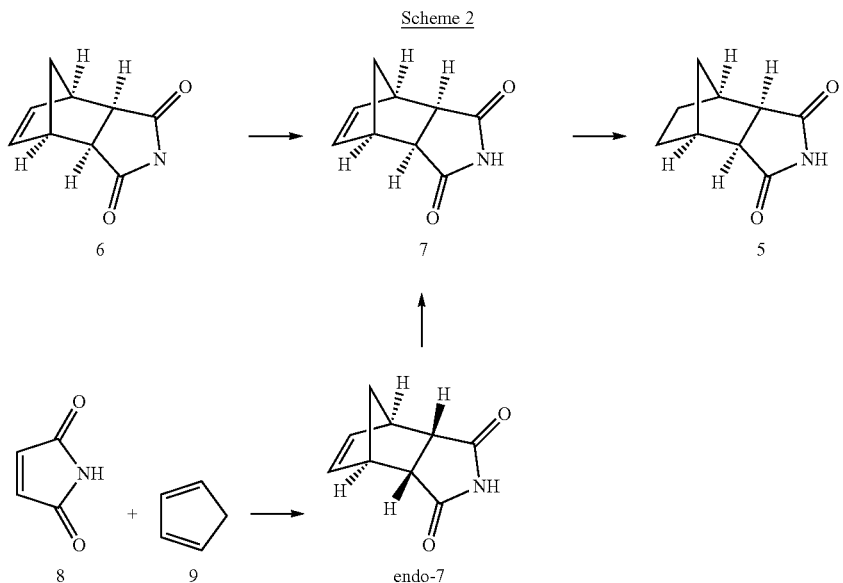

Scheme 2

WO2011062284 reports the preparation of intermediate 7 from anhydride 6 in 30% aqueous ammonia. This procedure requires very long reaction times (about 5 days), the evaporation of large amounts of water and a crystallization, and provides rather low yields, all to the detriment of the economy and productivity of the process.

J. Am. Chem. Soc., 1944, 66, 404-407 discloses the synthesis of intermediate 7 by reacting 6 with an excess of ammonium carbonate at high temperatures (200° C.) to obtain the imide after crystallisation, with a yield below 50%. The reaction involves the production of a large amount of gas which, together with the high temperatures required, makes this procedure unsuitable for industrial production both from the economic standpoint and in terms of safety. The same article describes the preparation of intermediate 7 by direct reaction between the molten anhydride 6 and gaseous ammonia, followed by crystallisation to obtain the desired product with low yields (<50%). Said reaction also has technical and safety difficulties when scaled up for industrial production.

Beilstein J. Org. Chem. 2009, 5, No. 81 discloses the preparation of the endo diastereoisomer of intermediate 7 (endo-7) in the presence of an excess of ammonium acetate in acetic acid as solvent (Scheme 3). The reaction is carried out at 140° C. for four days, and the product is isolated by extraction after complete evaporation of the solvent. This procedure not only involves very long times, but also problems relating to evaporation of the solvent and its subsequent management as waste, which make it unattractive from the industrial standpoint.

Scheme 3

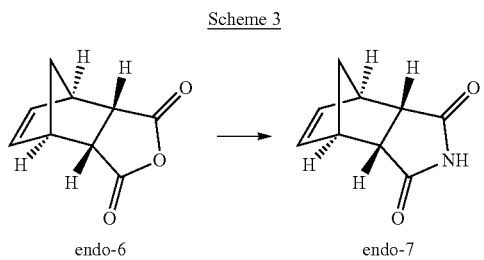 [SMILES: O=C1OC(=O)[C@H]2[C@@H]1[C@H]1C=C[C@H]2C1 ; O=C1NC(=O)[C@H]2[C@@H]1[C@H]1C=C[C@H]2C1]

endo-6    endo-7

The preparation of compounds similar to intermediate 7 is described in *Heterocycles,* 2006, 88, 2259-2267. The authors state that cyclic imides can be prepared from the corresponding anhydrides by reaction with ammonium chloride in the presence of considerable amounts of N,N-dimethylaminopyridine (DMAP), which acts as catalyst (about 20-50% molar compared with the substrate to be converted), or with ammonium acetate, under the effect of microwaves, also demonstrating that the reaction does not take place when a conventional heating system is used. The authors only describe the experimental procedure that uses ammonium chloride in the presence of DMAP; the reaction with ammonium acetate is not described. The reaction with $NH_4Cl$/DMAP gives medium-high yields (about 80-90%), but microwave technology, purifications by column chromatography and the use of large amounts of DMAP as catalyst, involving considerable disadvantages in terms of cost and purification of the product, make the procedure unattractive at industrial level, due to its cost and environmental impact.

Intermediate 7 can be obtained by Diels-Alder reaction between maleimide 8 and cyclopentadiene 9, which mainly gives the endo-7 isomer, and numerous successive isomerisations with gradual enrichment of the exo isomer by crystallisations at the expense of the final yield and production times. The synthesis route is reported in IPCOM000204532D, but without experimental data. The isomerisation of similar compounds is reported in EP0297078, and involves the use of high temperatures.

DESCRIPTION OF THE INVENTION

The use of inorganic bases insoluble in the reaction medium able to promote the complete formation of intermediate 4, neutralising the acid equivalent that forms during the reaction between 2 and 3, is disclosed in the present invention. The use of insoluble inorganic bases which, since they are not present in solution, are unable to promote the decomposition of intermediate 2, allows to employ stoichiometric amounts of reagents, ensuring high yields and considerably reducing the presence of impurities undetectable by UV detectors. Among the inorganic bases, magnesium and calcium oxides and hydroxides have suitable characteristics for use to neutralise the acid that forms in the formation reaction of intermediate 4, as they are insoluble and cheap.

The preparation of intermediate 7 from the corresponding anhydride 6 in the presence of an ammonium carboxylate as ammonia synthon in the absence of solvent, and the subsequent hydrogenation of 7 to give intermediate 5, is also disclosed in the present invention.

The use of ammonium carboxylates in the absence of solvent provides high yields and purities, preventing any by-products to form during the isolation step of the product and the use of organic solvents. The use of ammonium carboxylates in the synthesis of 7 permits a cost saving and a lower environmental impact with a simple, fast procedure suitable for industrial use.

DETAILED DESCRIPTION OF THE INVENTION

The object of the present invention is a process for the preparation of Lurasidone from (1R,2R)-cyclohexane-1,2-diyldimethanol 1, which comprises the following steps:
a) mesylation of 1 to give (1R,2R)-1,2-bis(methanesulfonyloxymethyl)cyclohexane 2;
b) reaction of 2 with 3-(piperazin-1-yl)benzo[d]isothiazole 3 in an organic solvent in the presence of a calcium or magnesium oxide or hydroxide, to give (3aR,7aR)-4'-(benz[d]isothiazol-3-yl)octahydrospiro[2H-isoindol-2,1'-piperazinium] methanesulfonate 4;
c) reaction of 4 obtained in step b) with (3aR,4S,7R,7aS) hexahydro-1H-4,7-methanoisoindolo-1,3(2H)-dione 5 to give Lurasidone.

In step a), intermediate 2 is prepared in the presence of an organic solvent, such as dichloromethane, acetonitrile, acetone, methyl isobutyl ketone, ethyl acetate or toluene, preferably dichloromethane or methyl isobutyl ketone, in the presence of a tertiary amine, preferably triethylamine, diisopropylethylamine, pyridine or lutidine. Methanesulfonic anhydride and mesyl chloride, preferably mesyl chloride, can be used as mesylating agents.

Step b) takes place in the presence of an organic solvent such as acetonitrile, ethanol, propanol or isopropanol, preferably isopropanol, or of a mixture of methyl isobutyl ketone, isopropanol and acetonitrile, in the presence of a calcium or magnesium oxide or hydroxide, such as calcium oxide, magnesium oxide, calcium hydroxide or magnesium hydroxide, preferably calcium hydroxide. Intermediate 4 is isolated in the presence of a solvent such as heptane, diisopropyl ether, toluene or xylene, preferably toluene.

Step c) is carried out in the presence of an organic solvent such as heptane, toluene or xylene, preferably toluene, in the presence of an inorganic base such as potassium carbonate or sodium carbonate, preferably potassium carbonate. Lurasidone is then isolated by the methods previously reported in the literature.

In one embodiment of the invention, intermediate 5 used in step c) is obtained by a process comprising the following steps:
d) reacting (3aR,4R,7R,7aS)-3a,4,7,7a-tetrahydro-4,7-methanoisobenzofuran-1,3-dione 6 in the presence of one or more ammonium C1-C6 carboxylates in the absence of solvents, at the melting temperature of the mixture, to give the intermediate (3aR,4S,7R,7aS)tetrahydro-1H-4,7-methanoisoindolo-1,3(2H)-dione 7;
e) hydrogenation of 7 to give 5.

In step d), ammonium acetate is preferably used as ammonium C1-C6 carboxylate.

In step e), intermediate 5 is prepared in an organic solvent or mixtures of solvents selected from methanol, ethanol and ethyl acetate, preferably methanol or ethanol, in the presence of hydrogen and a heterogeneous catalyst based on palladium or platinum, preferably palladium, more preferably palladium supported on carbon.

According to a preferred embodiment of the invention, Lurasidone is prepared as described below.

Typically, 1 molar equivalent of 1 is reacted with 1.8-3.0 molar equivalents of mesyl chloride, preferably 2.0-2.2 molar equivalents, in the presence of a tertiary amine, preferably triethylamine, in an amount ranging between 1.8-5.0 molar equivalents, preferably between 2.0-3.0 molar equivalents. The reaction is carried out in an organic solvent selected from acetonitrile, acetone, methyl isobutyl ketone, dichloromethane and toluene, preferably methyl isobutyl ketone, in the temperature range of −5° C. to 15° C., preferably at the temperature of 0° C.-5° C. 20-50 volumes of solvent are used, preferably 20-30 volumes compared with the amount of 1. The reaction is monitored by GC analysis. When the reaction is complete, water, typically 1-2 volumes of water compared with the volume of solvent, is added to the reaction mixture containing intermediate 2. The organic solution is separated from the aqueous phase and concentrated to 3-5 volumes, preferably 4 volumes. 0.9-1.1 molar equivalents of 3, preferably 1.0 molar equivalents compared with the amount of 2, are added, dissolved in 5-20 volumes of an organic solvent such as acetonitrile, ethanol, propanol or isopropanol, preferably isopropanol, or of a mixture of methyl isobutyl ketone, isopropanol and acetonitrile, preferably 5-10 volumes of solvent compared with the amount of 3. 0.9-5.0 molar equivalents of a calcium or magnesium oxide or hydroxide, such as calcium oxide, magnesium oxide, calcium hydroxide or magnesium hydroxide, preferably 2.0-3.0 molar equivalents of calcium hydroxide, are added to the resulting mixture. The mixture is then heated to reflux and left at that temperature for 12-24 hours, preferably 18 hours, monitoring the reaction with UPLC analysis. When the reaction is completed, the solid in suspension is filtered, and the resulting solution concentrated to a small volume. The addition of an apolar solvent such as toluene, xylene, heptane or diisopropyl ether, preferably toluene, causes the precipitation of intermediate 4, which is isolated with high yields and high purities (>98%) by filtration.

Intermediate 4 is then suspended in an organic solvent such as toluene, xylene or heptane, preferably toluene, and 0.9-1.8 molar equivalents of intermediate 5 are added, preferably 1.0-1.2 molar equivalents of intermediate 5 compared with intermediate 4, and 1.0-2.0 molar equivalents of an inorganic base such as potassium carbonate or sodium carbonate, preferably 1.1-1.3 molar equivalents of potassium carbonate. The mixture is then heated to a temperature ranging between 95° C. and the boiling point of the mixture, preferably 105° C., and left at that temperature for 8-18 hours, preferably 15 hours, the reaction being monitored by UPLC analysis. When the reaction is complete, water, typically 0.2-0.5 volumes of water compared with the volume of solvent, is added to the reaction mixture, and the mixture separates. The organic solution is then concentrated and the residue treated with a solvent such as ethanol, propanol or isopropanol, typically isopropanol, to give Lurasidone, or treated with a solution of HCl to give Lurasidone hydrochloride, in yields exceeding 98% and purities, measured by HPLC; exceeding 99%.

According to a preferred embodiment of the invention, intermediate 5 is prepared as described below.

Typically, 1 molar equivalent of anhydride 6 and 0.9-10 molar equivalents of one or more ammonium C1-C6 carboxylates, preferably 1.0-5.0 molar equivalents of ammonium acetate, are heated to the melting temperature of the mass and until the complete dissolution of anhydride 6. The reaction is monitored by GC analysis. When the reaction is complete, water is added to the mixture, preferably 2-3 volumes compared with the amount of ammonium carboxylate, and the solid that precipitates is isolated by filtration, to obtain intermediate 7 with quantitative yields (>98%) and high purity (>98%).

Intermediate 7 is then dissolved in 5-50 volumes of an organic solvent such as methanol, ethanol, isopropanol and ethyl acetate, preferably 8-10 volumes of methanol. A heterogeneous metal catalyst such as PdO, Pd supported on carbon, Pd supported on silica, $PtO_2$, Pt supported on carbon or Pt supported on silica, preferably 0.01-0.03 weights of Pd supported on carbon compared with the amount of intermediate 7, is added to this solution. The mixture is then reacted in hydrogen atmosphere, and the reaction is monitored by GC analysis. When the reaction is complete, the reaction mixture is concentrated and product 5 is isolated with quantitative yields (>98%) and high purity (>98%) by precipitation, adding water, typically 2-5 volumes of water compared with the initial amount of intermediate 7.

The process according to the invention is particularly advantageous as it is characterised by high yields and high purities of both the intermediates and the end product (Lurasidone or Lurasidone hydrochloride).

The process of the invention makes use of very cheap reagents of low toxicity, such as ammonium acetate and calcium hydroxide, thus allowing easy isolation of the synthesis intermediates and reduction of the environmental impact of the process.

In the preparation of intermediate 5 via intermediate 7, using an ammonium carboxylate as reaction medium, the yields and purities are increased and the preparation times of the intermediate reduced, avoiding the use of gaseous ammonia or high-pressure autoclaves or the use of expensive and/or pollutant organic solvents, thus considerably simplifying the work-up and product isolation steps. The simplicity and speed of the procedure makes it suitable for industrial use.

The synthesis of intermediate 4, carried out in the presence of an inorganic base which is inexpensive and poorly soluble or reactive, such as calcium hydroxide, allows the use of stoichiometric amounts of reagents, unlike the procedures published to date, wherein an excess of the expensive intermediate 2 or an excess of piperazine derivative 3, also relatively expensive, are used. The possibility of easily separating the inorganic base, using an insoluble calcium salt, and isolating intermediate 4 (a water-soluble quaternary ammonium salt) with high purity, leads to the production of a Lurasidone or Lurasidone hydrochloride with a purity exceeding 99% measured by HPLC.

The invention is illustrated in detail in the following examples.

EXAMPLES

Example 1

Synthesis of 7

A mixture of anhydride 6 (39.56 g, 0.241 mol) and ammonium acetate (55.73 g, 0.723 mol) is heated to 135° C. The resulting liquid is then stirred at 135° C. until the reaction is complete. The liquid is cooled and water (200 ml) is added in about half an hour. The resulting suspension is then cooled, and the white solid is centrifuged and washed with 100 ml of water to obtain imide 7 as a white solid (dry weight 39.34 g, yield 100%, purity [GC] 99.77%).

Example 2

Synthesis of 5

In an autoclave, 2 g of palladium on carbon (10% w/w 50% $H_2O$) and imide 7 (34.6 g, 0.212 mol) are suspended in methanol (600 ml). The autoclave is then closed and inertized with nitrogen, and hydrogen (8 atm) is introduced. The reaction is monitored by hydrogen consumption and by GC. When the reaction is complete, the solution is concentrated to a small volume, and water (200 ml) is added to the resulting suspension in about half an hour. The suspension is then cooled, and the white solid is filtered and washed with 25 ml of water to obtain imide 5 (dry weight 31.8 g, yield 91%, purity [GC] 99.98%).

Example 3

Synthesis of 4

Intermediate 1 (13.5 g, 96.3 mmol) is dissolved in a mixture of methyl isobutyl ketone (400 ml) and triethylamine (50 ml). The solution is then cooled at 0° C. to 5° C., and mesyl chloride (14.9 ml, 192 mmol) is added drop wise. After the addition, the mass is stirred until the reaction is complete, and water (400 ml) is added. The two phases are then separated, and the organic phase is concentrated to obtain a solution containing 26.10 g of 2, yield 92.8%.

A solution of 3 (19.1 g, 86.9 mmol) in isopropyl alcohol (300 ml) and calcium hydroxide (19.2 g, 260 mmol) is added to this solution. The reaction is then heated at reflux temperature for 20 hours, and monitored by UPLC. When the reaction is complete, the mixture is left to cool at room temperature and the salts are filtered through a Buchner filter and washed with isopropyl alcohol (55 ml). The organic solution is then concentrated, and toluene (85 ml) is added to the suspension. The solid is then filtered through a Buchner funnel and washed with toluene (40 ml) to obtain 4 as a white solid, 35.74 g, yield 97.1% from intermediate 2, purity [HPLC] 99.72%.

Example 4

Synthesis of Lurasidone

Intermediate 4 (32.2 g, 76.1 mmol), intermediate 5 (13.83 g, 83.7 mmol) and potassium carbonate (12.62 g, 91.3 mmol) are suspended in toluene (300 ml), and the resulting suspension is heated at 105° C. for 15 h, the reaction being monitored by UPLC. When the reaction is complete, the mixture is left to cool at room temperature and water (100 ml) is added. The phases are separated, the organic solution is concentrated to a small volume, and Lurasidone is isolated as the hydrochloride after treatment with HCl in an alcoholic solution 39.6 grams, yield 98.4%, purity [HPLC] 99.2%).

Example 5

Industrial Synthesis of 7

A mixture of anhydride 6 (70.0 kg, 426.4 mol) and ammonium acetate (98.6 kg, 1279.2 mol) is heated to 135° C. The resulting liquid is then stirred at 135° C. until the reaction is complete. The liquid is cooled and water (360 l) is added in about half an hour. The resulting suspension is then cooled, and the white solid is centrifuged and washed with 180 l of water to obtain imide 7 as a white solid (dry weight 68.8 kg, yield 98.8%, purity [GC] 99.84%).

Example 6

Industrial Synthesis of 5

In an autoclave, 3.8 kg of palladium on carbon (10% w/w 50% $H_2O$) and imide 7 (68.8 kg, 421.3 mol) are suspended in methanol (1000 l). The autoclave is then closed and inertized with nitrogen, and hydrogen (8 atm) is introduced. The reaction is monitored by hydrogen consumption and by GC. When the reaction is complete, the solution is concentrated to a small volume, and water (200 ml) is added to the resulting suspension in about half an hour. The suspension is then cooled, and the white solid is centrifuged and washed with 50 l of water to obtain imide 5 (dry weight 63.6 kg, yield 91.4%, purity [GC] 99.99%).

Example 7

Industrial Synthesis of 4

Intermediate 1 (10.6 kg, 73.5 mol) is dissolved in a mixture of methyl isobutyl ketone (315 l) and triethylamine (35 l). The solution is then cooled to between 0° C. and 5° C., and mesyl chloride (11.7 l, 151 mol) is added in 60 minutes. After the addition, the mass is stirred until the reaction is complete, and water (315 l) is added. The two phases are then separated, and the organic phase is concentrated to obtain a solution containing 20.44 kg of 2, yield 92.6%.

A solution of 3 (14.9 kg, 68.1 mol) in isopropyl alcohol (235 l) and calcium hydroxide (15.1 kg, 204.3 mol) is added to this solution. The reaction is then heated at reflux temperature for 20 hours, and monitored by UPLC. When the reaction is complete, the mixture is left to cool at room temperature, and the salts are centrifuged and washed with isopropyl alcohol (43 l). The organic solution is then concentrated, and toluene (65 l) is added to the suspension. The solid is then centrifuged and washed with toluene (32 l) to obtain 4 as a white solid, 28.8 kg, yield 97.3%, purity [HPLC] 99.87%).

Example 8

Industrial Synthesis of Lurasidone

Intermediate 4 (28.8 kg, 66.2 mol), intermediate 5 (12.0 kg, 72.8 mol) and potassium carbonate (11.0 kg, 79.7 mol) are suspended in toluene (270 l), and the resulting suspension is heated at 105° C. for 15 hours, monitoring the reaction by UPLC. When the reaction is complete, the mixture is left to cool at room temperature, and water (90 l) is added. The phases are separated, the organic solution is concentrated to a small volume, and Lurasidone is isolated as the hydrochloride after treatment with HCl in isopropanol (34.4 kg, yield 98.3%, purity [HPLC] 99.49%).

The invention claimed is:
1. A process for the preparation of Lurasidone starting from (1R,2R)-cyclohexane-1,2-diyldimethanol 1 which comprises the following steps:
   a) mesylating 1 to give (1R,2R)-1,2-bis(methanesulfonyloxymethyl)cyclohexane 2;

b) reacting 2 with 3-(piperazin-1-yl)benz[d]isothiazole 3 in an organic solvent in the presence of a calcium or magnesium oxide or hydroxide, to give (3aR,7aR)-4'-(benz[d]isothiazol-3-yl)octahydrospiro[2H-isoindol-2,1'-piperazinium] methanesulfonate 4;

c) reacting 4 obtained in step b) with (3aR,4S,7R,7aS) hexahydro-1H-4,7-methanoisoindole-1,3(2H)-dione 5 to give Lurasidone.

2. The process according to claim 1 wherein step b) is effected in the presence of calcium hydroxide.

3. The process according to claim 1 wherein in step b) 0.9-1.1 molar equivalents of 3 with respect to 2, are used.

4. The process according to claim 1 wherein in step b) the organic solvent is selected from the group consisting of acetonitrile, ethanol, propanol, isopropanol, or a mixture of methyl isobutyl ketone, isopropanol and acetonitrile.

5. The process according to claim 1 wherein intermediate 5 used in step c) is obtained with a process comprising the following steps:

d) reacting (3aR,4R,7R,7aS)-3a,4,7,7a-tetrahydro-4,7-methanoisobenzofuran-1,3-dione 6 in the presence of one or more ammonium C1-C6 carboxylates in the absence of solvents at the mixture melting temperature, to give (3aR,4S,7R,7aS)tetrahydro-1H-4,7-methanoisoindole-1,3(2H)-dione 7;

e) hydrogenating 7 to give 5.

6. The process according to claim 5 wherein in step d) 0.9-10 molar equivalents of one or more ammonium C1-C6 carboxylates, for 1 molar equivalent of 6, are used.

\* \* \* \* \*